US006689113B2

(12) United States Patent
Boulanger et al.

(10) Patent No.: US 6,689,113 B2
(45) Date of Patent: *Feb. 10, 2004

(54) SANITARY ABSORBENT ARTICLE WITH POSITIONING FLAPS CAPABLE OF GATHERING THE UNDERGARMENT TO PROTECT AGAINST WETTING

(75) Inventors: Roger Boulanger, Ste-Julie (CA); Pramod Mavinkurve, Princeton, NJ (US); Tara Glasgow, New Hope, PA (US); Anthony Ng, East Brunswick, NJ (US); Arnie Lingertat, New Hope, PA (US)

(73) Assignee: Johnson & Johnson Inc., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/800,348

(22) Filed: Mar. 6, 2001

(65) Prior Publication Data

US 2001/0009992 A1 Jul. 26, 2001

Related U.S. Application Data

(60) Division of application No. 08/996,141, filed on Dec. 22, 1997, now Pat. No. 6,602,235, which is a continuation-in-part of application No. 08/772,343, filed on Dec. 20, 1996, now abandoned.

(51) Int. Cl.[7] .................................................. A61F 13/15
(52) U.S. Cl. ............................ 604/385.04; 604/385.01; 604/385.28; 604/386; 604/387

(58) Field of Search ....................... 604/385.01, 385.03, 604/385.04, 386, 387, 389, 390, 385.28

(56) References Cited

U.S. PATENT DOCUMENTS

| 4,900,320 | A | * | 2/1990 | McCoy ....................... 604/387 |
| 5,344,416 | A | * | 9/1994 | Niihara .................... 604/385.1 |
| 5,354,400 | A | | 10/1994 | Lavash et al. |
| 5,391,162 | A | * | 2/1995 | Widlund et al. ......... 604/385.2 |
| 5,542,941 | A | * | 8/1996 | Morita .................... 604/385.1 |
| 5,591,147 | A | * | 1/1997 | Couture-Dorschner et al. .. 604/369 |
| 5,620,430 | A | * | 4/1997 | Bamber ................... 604/385.2 |
| 5,649,917 | A | * | 7/1997 | Roberts et al. .......... 604/385.1 |
| 5,714,027 | A | * | 2/1998 | Taub .......................... 156/204 |

FOREIGN PATENT DOCUMENTS

| WO | WO 92/07536 | 5/1992 |
| WO | WO 94/12135 | 6/1994 |

* cited by examiner

*Primary Examiner*—Weilun Lo
*Assistant Examiner*—Jacqueline F Stephens

(57) ABSTRACT

The present invention relates to a sanitary absorbent article such as a sanitary napkin that has the ability to protect the undergarment of the wearer from being soiled by menstrual liquid. The sanitary napkin has a main body with panels that originate from its longitudinal side edges. A distal end of each panel that is continuous with the respective longitudinal side edge is folded underneath and affixed to the barrier later of the main body to form a looping member and a freely extending flap. As a result the effective affixation point of each flap is located inwardly of the respective side edge of the main body.

22 Claims, 6 Drawing Sheets

SANITARY ABSORBENT ARTICLE WITH POSITIONING FLAPS CAPABLE OF GATHERING THE UNDERGARMENT TO PROTECT AGAINST WETTING

RELATED APPLICATIONS

This Application is a continuation in part of U.S. Ser. No. 08/772,343 filed Dec. 20, 1996, now abandoned and a divisional of U.S. Ser. No. 08/996,141 filed Dec. 22, 1997, now U.S. Pat. No. 6,602,235.

FIELD OF THE INVENTION

The present invention relates to structures designed for absorbing body exudate. More particularly, the invention provides an improved sanitary absorbent article featuring an enhanced capability to protect the undergarment from wetting.

BACKGROUND OF THE INVENTION

A sanitary napkin typically comprises an elongated main body that is intended to be placed in the crotch portion of the undergarment so it remains in contact with the perineal region of the wearer. The sanitary napkin includes a liquid-permeable cover layer located over an absorbent core that is designed to collect and store body exudate discharged by the user. Optionally, a transfer layer may be placed between the cover layer and the absorbent core. To prevent liquid collected in the absorbent core from soiling the undergarment of the wearer a liquid-impermeable barrier layer is located under the absorbent core.

Experimental procedures conducted on sanitary napkin designs have demonstrated that product failures can often be traced to the inability of the cover layer of the sanitary napkin, which is in contact with the perineal region of the wearer, to effectively capture on contact the discharge of body exudate. If liquid remains on the cover layer for an extended period of time droplets are likely to run off of the surface of the cover layer and leak past the edge of the sanitary napkin. The precise point of leakage depends primarily upon the posture of the wearer. For example, when a wearer lies horizontally in a supine position, the gravitational forces induce the liquid to travel longitudinally on the sanitary napkin and to accumulate on the rear longitudinal end portion. To avoid saturation and overflow leakage at that area, products with improved absorbency at the critical site have been developed during the past recent years. An example is the sanitary napkin available from Johnson & Johnson Inc. under the trade designation STAYFREE PRIMA Ultra Thin/Long Maxi. This product features a long body that progressively widens toward the rear so as to offer an increased liquid-acquisition surface area.

Alternatively, sanitary napkins designed primarily for daytime use have been found to leak mostly at the longitudinal sides of the napkin. This is primarily due to the normally erect or sitting positions of the wearer which causes the liquid to accumulate in the central area of the napkin which has a reduced width due to compressive forces exerted by the wearer's legs. As a consequence, a much smaller surface area is available to the liquid for penetrating the absorbent structure.

In an attempt to reduce the possibility of undergarment or garment wetting resulting from side failures, several solutions have been proposed by the industry. One attempt to solve this problem is to provide the main body of the sanitary napkin with wings or flaps which extend from the longitudinal sides of the napkin and are folded about the edges of a crotch portion of a wearer's undergarment to form upstanding walls which provide a shielding function. These flaps originate from the side edges of the main body and are provided with adhesive zones allowing the flaps to be secured against the outside surface of the undergarment. Thus, in the event that droplets of menstrual fluid leak past the side edges of the main body of the napkin, the undergarment will be protected from the liquid by virtue of the flaps.

This approach, however, presents a number of drawbacks. For example, the addition of side flaps to a sanitary napkin increases the manufacturing costs associated with the sanitary napkin. In addition, in an attempt to provide enhanced protection against side leakage, manufacturers have substantially increased the width of the flaps, measured along the length of the napkin, to provide wide flaps. Major difficulties observed with sanitary napkins provided with such wide flaps are the stresses created when fitting the flap about the curved edges of an undergarment and the inability of the flaps to conform well to the edges of the undergarment. Since the edges of the undergarment are outwardly curved from the narrow central crotch portion to become wider as the undergarment encircles the legs, wide flaps, when folded about the edges of the crotch portion of the undergarment will have a tendency to detach and/or form wrinkles which cause irritation and discomfort by chafing the inner thighs of the wearer and are also detrimental to the adhesive bond between the flaps and the undergarment, resulting in a further likelihood of detachment of the flaps from the undergarment. One possibility to solve this problem is to use a longitudinally extensible or elastic material to form wide flaps which are more comfortable to the shape of the undergarment edges.

Under a different approach the main body of the sanitary napkin is provided with flaps that are affixed to the barrier layer, i.e. on the garment facing side of the napkin, at a point located inwardly of the respective side edges of the sanitary napkin. The flaps may be adhered to the underside of the wearer's undergarment or may be sufficiently long so they completely encircle the crotch portion of the undergarment and they are retained to one another in overlapping relationship. Since the flaps originate inwardly of the respective side edges, they have the effect of gathering the undergarment so that it remains inward of the longitudinal side edges of the main body. Thus, it is the body-facing side of the main absorbent body that provides the primary undergarment shielding function while the flaps positively prevent the edges of the undergarment from extending over the cover layer of the main body where they are subject to wetting. Examples of sanitary napkins constructed in accordance with this concept are described in U.S. Pat. No. 4,900,320 granted to McNeil-PPC on Feb. 13, 1990, which is incorporated herein by reference in its entirety.

The embodiments described in the U.S. Pat. No. 4,900,320 are, however, difficult to manufacture on high speed automated equipment because the flaps are formed separately of the main body and then affixed to the barrier layer of the main body in order to form the sanitary napkin. This requires a more complex manufacturing process that translates in higher production costs. Indeed, the industry has recognized that the most economical way of mass producing sanitary napkins is to form the flaps of the individual products integrally with the barrier layer, the cover layer or with both layers.

OBJECTS AND STATEMENT OF THE INVENTION

An object of the invention is to provide a sanitary napkin that is capable of protecting the undergarment of the wearer against wetting.

Another object of the invention is to provide a sanitary napkin that offers enhanced protection against undergarment wetting and which, at the same time, is easy to mass produce at low cost.

Yet, another object of the invention is to provide a method for manufacturing the aforementioned sanitary napkin.

As embodied and broadly described herein, the invention provides a sanitary absorbent article adapted to be worn in a crotch portion of an undergarment, comprising:

(A) a main body having opposed longitudinal side edges and a longitudinal centerline, said main body including: a body-facing fluid-permeable upper layer intended for placement against a perineal region of a wearer, a garment-facing fluid-impervious lower layer, and an absorbent layer between the upper layer and the lower layer; and (B) a first panel and a second panel, each panel being integrally formed from the upper layer, the lower layer or a combination of both the upper layer and the lower layer, each panel having a proximal end adjacent to and extending from respective opposite longitudinal side edges of said main body and a distal end freely extending laterally from the proximal end of said panel, the proximal end and the distal end defining therebetween a body portion, the body portion further comprising a longitudinally extending folding axis which is substantially parallel to said longitudinal side edge, each panel being capable of being folded about said folding axis onto itself such that the distal end of the panel projects laterally inward towards the longitudinal centerline of said main body on a garment-facing side of the sanitary absorbent article, each panel further including:

(i) a juncture zone located within the body portion adjacent the proximal end of said panel, the juncture zone attaching a portion of said panel to the barrier layer inwardly from the longitudinal side edge of said main body, the juncture zone simultaneously defining a looping member and a freely extending flap (ii) the looping member being adjacent to and substantially parallel with the longitudinal side edges of the main body and being defined by a portion of the body portion of said panel between the proximal end and the juncture zone and including the folding axis therebetween, the looping member being substantially unitized;

(iii) each flap being defined by a portion of the body portion of said panel between the juncture zone and the distal end and being capable of being folded about a side edge of the crotch portion of the undergarment, each flap further including a first transverse end and a second transverse end, the second transverse end being opposite the first transverse end and defining therebetween a flap width in a direction substantially parallel to the longitudinal side edges of the main body, (iv) each flap having means for holding at least a portion of one edge of the undergarment inwardly of said longitudinal side edge of the main body when the flap is in a folded condition about the side edge of the undergarment, wherein the juncture zone of the first panel is separated from the juncture zone of said second panel by a distance which defines an undergarment allowance and the undergarment allowance, as measured at the respective transverse ends of the flaps, gathers the edges of the undergarment inward toward the longitudinal centerline of the main body in an amount less than 25% of the original width of the undergarment.

As embodied and broadly described herein, the present invention provides a method of manufacturing a plurality of sanitary absorbent articles comprising the steps of:

providing a continuous web of fluid pervious material having a width defined between opposite longitudinal sides, forming a plurality of discrete elongated absorbent structures defined by an outer periphery having an upper surface and a lower surface, opposite longitudinal sides and opposite transverse ends, the absorbent structure being formed from fibrous absorbent materials, adhering the upper surface of the absorbent structures to the fluid pervious material such that each absorbent structure is in a longitudinally spaced apart position with respect to an adjacent absorbent structure, providing a continuous web of a fluid impervious material having a width defined between opposite longitudinal sides, adhering the lower surface of the absorbent structures to the fluid impervious material, sealing the fluid pervious material to the fluid impervious material around the outer periphery of each absorbent structure forming a flange seal, cutting the upper and lower surfaces along their respective longitudinal sides to form a pair of opposite side panels continuous with either the upper surface, the lower surface or both the upper surface and the lower surface, the side panels projecting laterally outward from a central potion of the absorbent structure, each panel having a base portion and a flap portion, the base portion being longer than the flap portion in a direction substantially parallel to the longitudinal sides of the absorbent structure, each panel further including a proximal end that is adjacent the absorbent structure, a distal end remote from the absorbent structure and a continuous body portion between the proximal end and the distal end;

folding the distal end of each panel under the main body;

affixing the base portion of the panel to the main body at a zone of juncture which is adjacent the proximal end of the panel so the panel remains in a folded condition, wherein the distal end is allowed to freely extend laterally inward thereby defining a freely extending flap and the body portion is located inwardly of the respective longitudinal side edge, cutting the upper and lower surfaces across their entire width to form a plurality of individual sanitary napkins.

In a most preferred embodiment, the sanitary absorbent article is a sanitary napkin designed for absorbing menstrual liquid. The sanitary napkin includes a main body for placement against the perineal region of the wearer a pair of first liquid barriers extending substantially along the entire longitudinal side edges of the main body, the first liquid side barriers being formed by the looping members and a pair of flaps projecting laterally from the garment facing side of the main body, inward from the longitudinal side edges, the flaps being adapted to encircle the crotch portion of the undergarment. The main body is a layered structure including an upper, liquid-permeable cover layer, an absorbent system underneath the cover layer and a liquid-impermeable barrier layer below the absorbent system. The cover and the barrier layers may be peripherally sealed to one another to completely enclose the absorbent system.

The absorbent structure is generally an absorbent pulp fluff material, and may optionally comprise a dual-layer structure, including a highly porous transfer layer on top of a sphagnum moss absorbent core. It will be appreciated, however, that different absorbent systems can be used without departing from the spirit of the invention.

The panels originate from a central portion of the longitudinal side edges of the main body. Each panel has a base portion located at a proximal end that is continuous with and adjacent to the respective side edge of the main body, and flap portion a distal end continuous with the proximal end and which extends laterally outward from the longitudinal sides of the absorbent article. The base portion has a length longer than the flap portion. The distal end of the panel is folded underneath the barrier layer, i.e. on the garment facing surface of the absorbent article, and the panel is affixed to the barrier layer along the base portion at a juncture zone which is adjacent to the proximal end and inward of the longitudinal sides of the absorbent article so it remains in a folded condition. The folded portion of the flap forms a looping member which, when affixed to the barrier adjacent the flange, forms a first liquid barrier along the longitudinal sides of the napkin. The distal end thus forms a flap which extends inwardly from the respective side edge toward the longitudinal centerline of the absorbent article and is affixed inwardly of the side edge. As a result, when the flaps are folded about the crotch portion of the undergarment, they maintain or gather the undergarment sufficiently so the portions of the side edges of the undergarment located in the central area of the main body (those portions of the side edges of the undergarment are most susceptible of being wetted if failure occurs) remain within a boundary defined by the longitudinal side edges of the absorbent article. Accordingly, the main body of the absorbent article provides the major shielding function and protects the undergarment from being wetted and soiled with menstrual liquid.

The portion of the panel between the proximal end and the juncture zone defines a looping member. In order to reduce the cost of manufacturing the article, the looping member may be substantially unitized. In this context the term "substantial unitized" is used to indicate that the layers forming the looping member and all other material contained therein are attached together over an appreciable portion thereof to form an integral whole. The presence of unattached or free-floating structures within the looping member would significantly increase the cost of manufacture of the article.

Another advantage of this sanitary napkin configuration is the ability of the longitudinal side portions of the main body to resist the tendency to slope downwardly due to tension imparted by the flaps. That is, since the body portion of each flap originates inwardly of the respective side edge of the absorbent article, any tension which arises when the flap is fastened to the undergarment, will act against the barrier layer inwardly of the side edge. As a consequence, the peripheral edge portions of the main body are less likely to slope downwardly by comparison to a design where the tension imparted by the flaps act solely on the side edges. As mentioned before, such downward sloping is undesirable because it permits liquid pooling on the cover layer to leak sideways under the effect of gravity.

As embodied and broadly described herein, the present invention further provides a sanitary napkin, comprising:
(A) a main body having opposed longitudinal side edges, said main body including:
   (i) a liquid-permeable cover layer,
   (ii) an absorbent layer underneath the liquid-permeable cover layer, and
   (iii) a liquid-impervious barrier layer below the absorbent layer, the cover layer and barrier layer being sealed about a peripheral edge margin to enclose the absorbent layer;
(B) a longitudinally extending looping member extending laterally outward from each respective longitudinal side edge, each looping member integrally formed from either the cover layer, the barrier layer, or both the cover layer and the barrier layer, the looping member being formed by folding at least one of said layers around and affixing the layer to the barrier layer at a juncture zone located inwardly of the respective longitudinal side edge;
(C) a pair of flaps on opposite sides of said main body, said flaps integrally formed from the looping member, said flaps being affixed to the barrier layer inwardly of the respective longitudinal side edge of the main body and projecting laterally from said main body in a direction generally transverse to the longitudinal side edges, each of said flaps including:
   (I) a distal end continuous with the respective juncture zone which attaches at least a portion of said flap to the barrier layer, the distal end being folded under the barrier layer and extending laterally inwardly in a direction away from the respective longitudinal side edge,
   (ii) a body portion retained to the distal end, the body portion being capable of being folded about a crotch portion of an undergarment on which the sanitary napkin is placed.

As embodied and broadly described herein the present invention further provides a method of manufacturing a sanitary napkin having a fluid-permeable cover layer, a fluid-impervious barrier layer, an absorbent core between the cover layer and the barrier layer, and flaps affixed to the barrier layer, comprising the steps of:
(A) adhering a first surface of the absorbent core to a surface of the fluid-permeable cover layer wherein the cover layer has a width which is greater than the width of the absorbent core;
(B) adhering a second surface of the absorbent core to a surface of the fluid-impervious barrier layer, wherein the barrier layer has a width substantially equivalent to the width of the cover layer;
(C) sealing the cover layer to the barrier layer around a peripheral edge margin of the absorbent core to form a flange seal;
(D) cutting the cover layer and the barrier layer outward of the flange seal in a pattern which defines a main body of a sanitary napkin having a pair of laterally extending panels, one panel extending from each respective longitudinal side of the main body of the sanitary napkin, the panels being integrally formed from either the cover layer, the barrier layer or both the cover layer and the barrier layer, the panels having a proximal end adjacent each respective longitudinal side edge of the sanitary napkin and a distal end extending laterally outward from the respective longitudinal side edge of the sanitary napkin;
(E) folding the panels along a folding axis under the barrier layer; and
(F) affixing the panels to the barrier layer along a juncture zone which is inward of the longitudinal side edges and underneath the main body of the sanitary napkin such that the distal end of the panels extend laterally inward toward a longitudinal centerline of the sanitary napkin thereby defining a pair of freely extending flaps.

DESCRIPTION OF A PREFERRED EMBODIMENT

Figure 1:
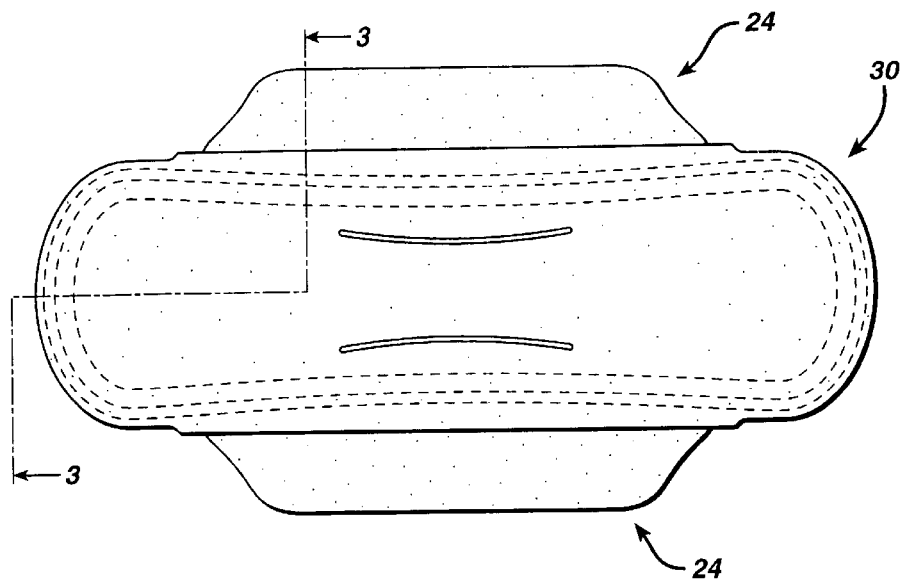
FIG. 1 is a top plan view of a sanitary napkin constructed in accordance with the present invention.
Figure 2:
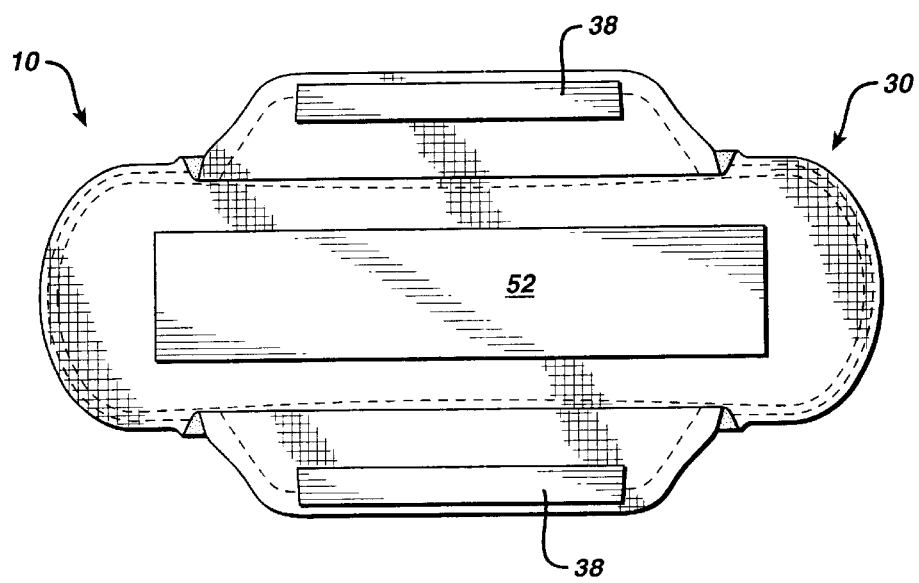
FIG. 2 is a bottom plan view of a sanitary napkin constructed in accordance with the present invention.
Figure 3:
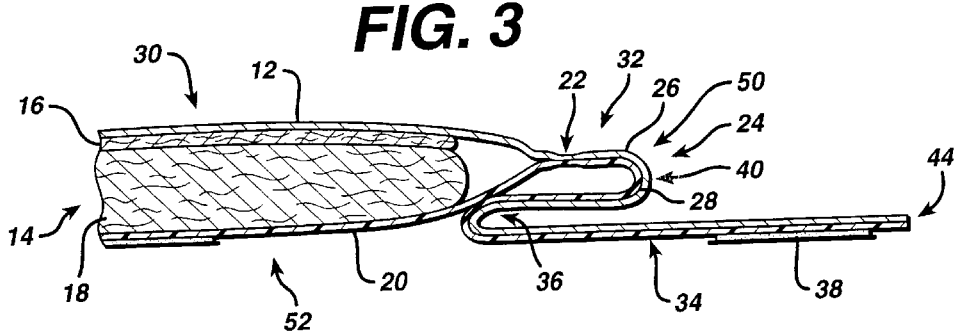
FIG. 3 is a cross-sectional view taken along line 3—3 in FIG. 1.

Referring now to the annexed drawings, more particularly to FIGS. 1, 2, and 3, the present invention provides a sanitary napkin which is designated comprehensively by the reference numeral 10 and which is characterized by the ability to better protect the undergarment of the wearer against wetting and soiling by menstrual liquid.

More specifically, the sanitary napkin 10 comprises a liquid-permeable cover layer 12 overlaying an absorbent system 14. The cover layer may be a relatively low density, bulky, high-loft non-woven web material. The cover layer 12 may be composed of only one type of fiber, such as polyester, or it may be composed of bicomponent fibers having a low melting point component and a high melting point component. The components of bicomponent fibers may be arranged with respect to each other as side by side or one surrounding another as a sheath around a core. Examples of low and high melting components are polyethylene and polyester, polypropylene and polyester, polyethylene and high melting polyester. The use of appropriate bicomponent materials results in a fusible non-woven fabric. Examples of such fusible fabrics are described in U.S. Pat. No. 4,555,430 issued Nov. 26, 1985 to Mays. Using a fusible fabric increases the ease with which the cover layer may be adhered to the adjacent transfer layer and/or to the barrier layer. Fibers may also be selected from a variety of natural and synthetic materials such as nylon, polyester, rayon (in combination with other fibers), cotton acrylic fiber and the like and combinations thereof.

The cover layer preferably has a relatively high degree of wettability, although the individual fibers comprising the cover may not be particularly hydrophilic. The cover material should also contain a great number of relatively large pores. This is because the cover layer is intended to absorb body fluid rapidly and transport it away from the body and the point of deposition. Preferably, the fibers which make up the cover layer should not lose their physical properties when they are wetted, in other words they should not collapse or lose their resiliency when subjected to water or body fluid. The cover may be treated, e.g. with surfactant and/or high energy discharge, e.g., corona discharge, to allow fluid to pass through it readily. Since the cover layer also functions to transfer the fluid quickly to the other layers of the absorbent structure, the cover is preferably wettable, hydrophilic and porous. Thus, when composed of synthetic hydrophobic fibers such as polyester or bicomponent fibers, the cover may be treated with a surfactant to impart the desired degree of wettability.

Alternatively, the cover layer 12 may be made of an apertured polymeric film. Because of the hydrophobicity and high porosity of apertured polymeric films, they quickly transfer body fluids deposited on the cover to the inner layers of the absorbent structure. Apertured films made of co-extruded polymers, examples of such being the RETICULON brand, which are described in U.S. Pat. No. 4,690,679 are useful as cover layers in the absorbent structures of this invention.

The cover layer 12 may be micro or macro embossed to improve the texture of the polymeric film and reduce the plastic "feel" of the cover against a wearer's skin. Cover layer may be optionally adhered to the lower absorbent layer to further enhance fluid transfer from the cover to the next layer.

Adjacent to the cover layer 12 on its inner side and bonded to the cover layer 12 is an absorbent system 14 which comprises an optional fluid transfer layer 16 and an absorbent core 18 which together form the absorbent system 14. The transfer layer 16 provides the means of quickly receiving body fluid from the cover layer 12 and holding it until slower absorbing absorbent core 14 has an opportunity to acquire the fluid. The transfer layer 16 is, preferably, more dense than and has a larger proportion of smaller pores than the cover layer 12. These attributes allow the transfer layer 16 to contain body fluid and hold it away from the outer side of the cover layer 12, thereby preventing the fluid from re-wetting the cover layer 12 and its surface. However, the transfer layer is, preferably, not so dense as to prevent the rapid passage of the fluid through the layer into the absorbent core.

Transfer layer 16 generally comprises fibrous materials, such as wood pulp, polyester, rayon, flexible foam, or the like, or combinations thereof. The transfer layer 16 may also comprise thermoplastic fibers for the purpose of stabilizing the layer and maintaining its structural integrity. Transfer layer 16 may be treated with surfactant on one or both sides in order to increase its wettability, although generally the transfer layer 16 is relatively hydrophilic and may not require treatment. Transfer layer 16 is preferably bonded on both sides to the adjacent layers, i.e. the upper cover layer 12 and the lower absorbent core 18.

Immediately adjacent to and bonded to transfer layer 16 is absorbent core 18. Absorbent core 18 is preferably a highly dense layer having a fine porosity. It has a large liquid holding capacity and it is extremely retentive. Absorbent core 18 may be generally rectangular having substantially straight parallel side margins, or may be contoured to adapt to the body of the wearer such as in an hourglass shape or a dog-bone shape. In addition, core 18 may contain one or more embossed channels which stabilize the absorbent article and enhance fluid transfer within the absorbent core by capillary action. In one embodiment, the absorbent core 18 comprises a cellulosic pulp fluff material. In another embodiment, the absorbent core 18 comprises a compressed sphagnum moss material. In yet another embodiment, the absorbent core 18 comprises a combination of a cellulosic pulp fluff material and a compressed sphagnum moss material. In accordance a preferred embodiment, a compressed sphagnum moss material is formed as a board by air or wet laying and calendering to obtain a relatively thin, i.e., from about 0.01 to 0.10 inch thick, relatively dense, i.e., from about 0.2 to 1.0 g/cm$^3$ sheet like structure. The structure may include a layer of Kraft tissue laminated on one or both surfaces of the sphagnum moss layer. Preferably, a fibrous component is admixed with the sphagnum moss material. The fibrous component is suitably a natural or synthetic textile fiber such as rayon, polyester, nylon, acrylic or the like, having a length of from about 0.30 to 1.5 inches and a denier of from about 1.0 to 5. The fibrous component may be present in an amount from about 2 to 20% by weight, most preferably from 4 to 8%. Absorbent core 18 may also comprise other components such as wood pulp, synthetic wood pulp, thermomechanical pulp, mechanically ground pulp, polymers, surfactants, conjugate fibers, fusible fibers, binders, sphagnum moss particles, deodorants, superabsorbents, and the like and combinations thereof.

Underlying absorbent system 14 is a barrier layer 20 comprising liquid-impervious film material so as to prevent liquid that is entrapped in the absorbent core from egressing the sanitary napkin and staining the wearer's undergarment. Most preferably, the barrier layer 20 is made of polymeric film, such as co-extruded EVA/polyethylene laminate which is both inexpensive and readily available. The film is capable of fully blocking the passage of liquid or gas that may emanate from the absorbent system 14. In a variant, breathable films may be used that allow passage of gases while blocking liquid.

Cover layer 12 and barrier layer 20 are joined along their marginal edge portions to form a peripheral seal line or flange 22 as illustrated in FIGS. 3–6 which encloses and maintains the absorbent system 14 captive.

Figure 10:
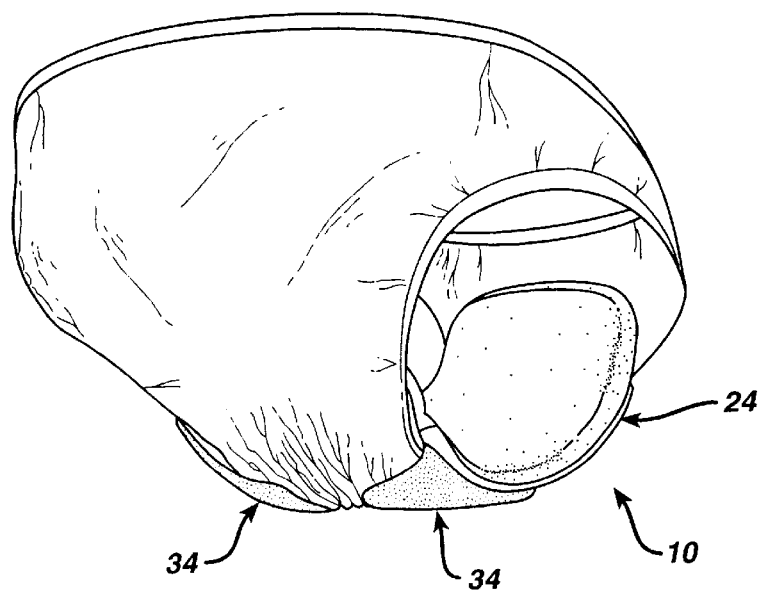
FIG. 10 is a perspective view of the sanitary napkin constructed in accordance with the present invention when placed in an undergarment.
Figure 11:
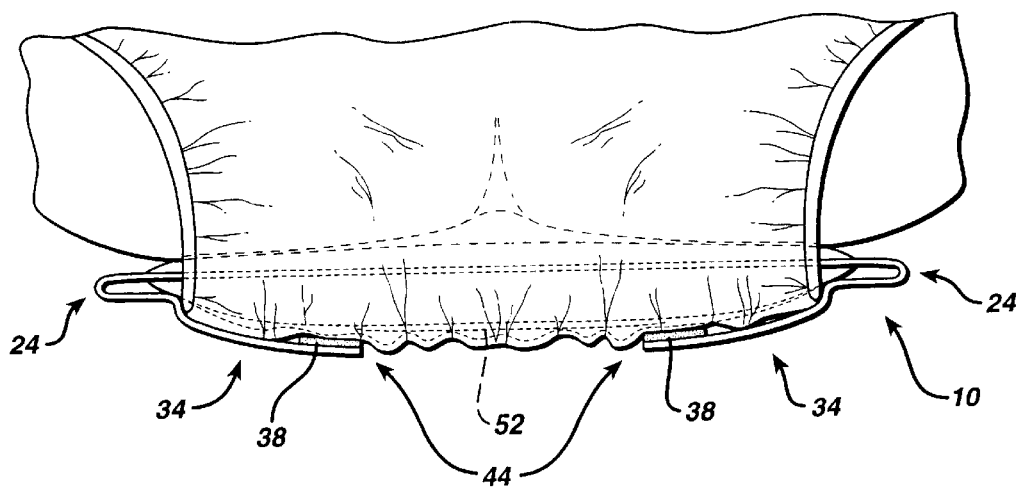
FIG. 11 is a cross-sectional view of the sanitary napkin constructed in accordance when the present invention when placed in an undergarment.
Figure 12:
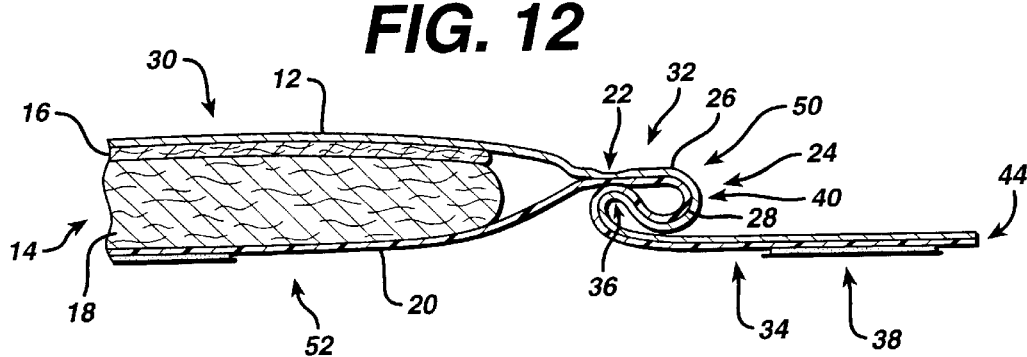
FIG. 12 is a cross-sectional view of another embodiment of a sanitary napkin constructed in accordance with the present invention taken along line 3—3 in FIG. 1.
Figure 13:
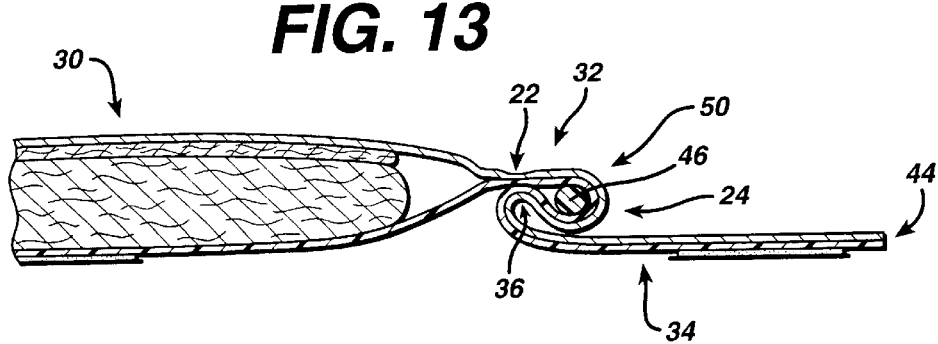
FIG. 13 is a cross-sectional view of another embodiment of a sanitary napkin constructed in accordance with the present invention taken along line 3—3 in FIG. 1.
Figure 14:
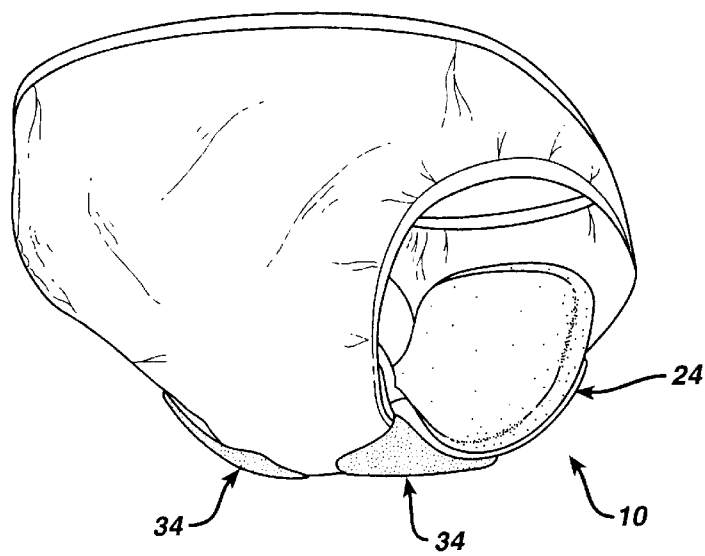
FIG. 14 is a perspective view of the sanitary napkin constructed in accordance with the present invention when placed in an undergarment.
Figure 15:
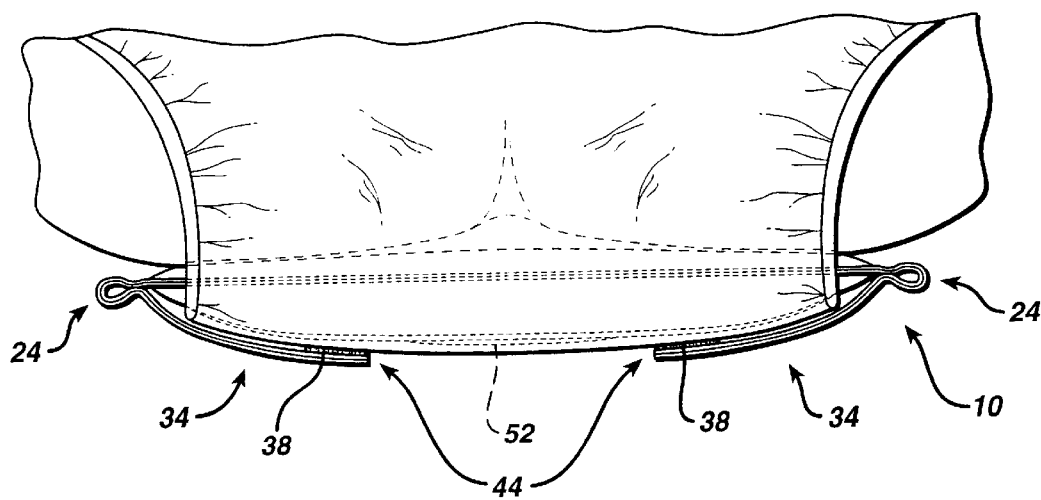
FIG. 15 is a cross-sectional view of the sanitary napkin constructed in accordance when the present invention when placed in an undergarment.

Sanitary napkin 10 further comprises a pair of panels 44 that extend laterally outward from the longitudinal edges of the napkin. Panels 24 are under the garment-facing side of the sanitary napkin and affixed to the barrier layer inward from a lateral edge of the sanitary napkin. The freely extending distal ends of the panels form outwardly extending flaps. Referring to FIGS. 10 and 11, in use, the sanitary napkin is placed in a crotch portion of an undergarment and the flaps are folded over the edges of a crotch portion of the undergarment whereupon the flaps maintain at least a portion of the edges of the crotch portion of the undergarment in a position which is inward from the longitudinal side edges of the sanitary napkin and underneath the main body, and preferably maintains at least a portion of the edges in a position underneath the absorbent system.

In order for the flaps to be attached to the wearer's undergarment in a comfortable manner, it has now been discovered that the flaps should not gather the undergarment in an amount which exceeds 25 percent of the original undergarment width as measured in the crotch region. More specifically, as is well known, the crotch region of an undergarment possesses a substantially parabolic shape wherein the center of the crotch is relatively narrow and then widens substantially in a direction towards both the front and rear panels of the undergarment. Thus, an absorbent article having flaps which are adapted to gather the edges of the crotch region of the undergarment towards the longitudinal centerline of the absorbent article will tend to gather the undergarment in those regions of the crotch which widen toward the front and rear of the undergarment. Accordingly, it is the transverse end regions of each flap (i.e. the corner regions of the flap adjacent the juncture zone which are folded around the edges of the wearer's undergarment) which will have the greatest tendency to alter or gather the normal edge of the undergarment inward towards the longitudinal centerline of the absorbent article. In accordance with the present invention, the distance between the flaps, as measured across the main body of the absorbent article from one juncture zone to an opposite juncture zone in a region proximate to the transverse ends of the flaps should not distort or gather the undergarment more than 25 percent of its original undistorted width, preferably less than 20 percent and most preferably less than 10 percent of the original undergarment width.

The flaps may be of a length sufficient to completely encircle the crotch portion of the undergarment or alternatively they may have a length which is sufficient to be adhesively secured to the garment side of the undergarment so as to gather the undergarment well within the boundary of the main body 30 of the sanitary napkin. As a result, the sides of the undergarment are retained under the sanitary napkin and thus shielded against wetting and/or staining.

The structure of each flap is best shown in FIGS. 2 and 3. The panels originate from their respective side edges of the main body 30 and include longer base portion adjacent the longitudinal sides of the sanitary napkin which tapers towards the distal ends of the panel. The panels may include a cover layer portion 26, continuous with the cover layer 12, or a barrier layer portion 28, continuous with the barrier layer 20 or both a cover layer portion 26 and a barrier layer portion 28. Optionally, the cover layer portion 26 may comprise a separate non-woven fabric to provide a softer texture and to eliminate the "plastic" feel generally associated with the use of apertured polymeric films.

The cover layer portion 26 and barrier layer 28 are peripherally united to the barrier layer portion 28 by the seal line 22 (shown in FIG. 3) adjacent the flange seal along the longitudinal sides of the napkin. The bond in seal line 22 may be made by means of adhesives, heat-bonding, ultrasonic bonding, radio frequency sealing, mechanical crimping, and the like and combinations thereof. Panel 24 may also comprise between cover layer portion 26 and barrier layer portion 28 additional material such as that of the absorbent core, the transfer layer, a fibrous highloft material, a resilient sheet of a polymeric foam material or combinations thereof.

Each panel 24 is comprised of a plurality of portions continuous with one another as hereinafter defined, a distal end 44 and a proximal end 32, defining therebetween a flap body portion 34 and a juncture zone 36 which is adjacent the proximal end 32. Proximal end 32 originates at a side edge toward a longitudinal centerline of the main body of the sanitary napkin. Juncture zone 36, defined between proximal end 32 and flap body portion 34 is in the form of a line substantially parallel to the side edge of main body 30. Intermediate proximal end 32 and flap body portion 34 is at least one folding axis 40 about which the panel is folded in an orientation under the barrier layer in a direction toward the longitudinal centerline of the sanitary napkin.

The panel 24 is affixed, at least in part, to the barrier layer 20 underneath the main body 30 at juncture zone 36 by means of adhesives, heat-bonding, ultrasonic bonding, radio frequency sealing, mechanical crimping, and the like and combinations thereof. The juncture zone may be a substantially straight line or alternatively may be in an arcuate shape either convex inward or convex outward with respect to the longitudinal centerline of the sanitary napkin.

The portion of the panel 24 between the proximal end 32 and the juncture zone 36 defines the looping member 50. The looping member 50 is substantially unitized. Where the flap is of a single layer construction, e.g. an extension of the cover layer, the looping member will generally be substantially unitized. Where the panel is of a multi-layer construction, it will be substantially unitized wherein the layers which form the looping member 50 are appreciably attached to one another. Any conventional method of attachment may be used. In FIGS. 3–6, the layers 26 and 28 are attached to one another over their entire facing-surface areas.

Flap body portion 34 is allowed to extend freely from the juncture zone 36 that is located inwardly of the respective side edge of the main body 30. As a result, the effective affixation point of the flap 34 is located inwardly of the longitudinal side edge. This presents a number of advantages. When the flaps 34 are folded to encircle the crotch portion of the undergarment, and depending upon the width of the crotch portion of the undergarment, the flaps 34 either compress and gather the undergarment material or simply maintain the undergarment material between the two opposite juncture zones 36. As a result, the undergarment is confined well within the boundary of the main body 30 that shields that portion of the undergarment from wetting. In a preferred embodiment, the affixation points in the juncture zone are at least 71 mm apart as measured from one flap to an opposite flap, more preferably at least 75 mm apart and most preferably between 75 and 85 mm apart. When the juncture zone in the form of a non-linear line, e.g. such as a convex curve, the distance between the affixation points should be determined at the opposite transverse end regions 70 and 71 of the flap.

In addition, since the effective affixation point of each flap 34 is located inwardly of the side edges of the absorbent article, this eliminates or substantially reduces the likelihood that the sides of the main body 30 will slope downwardly under the effect of tension communicated by the flaps. That is, if the tension vectors of the flaps act on the side edges of the absorbent article, it will be apparent that the main body will slope downwardly at the sides. Such downward sloping configuration is undesirable because it may induce liquid that has not immediately been absorbed through the cover layer 12 to leak sideways under the effect of gravity and unto the wearer's undergarment or garments. In accordance with the present invention, tension communicated to flaps which are attached inwardly of the longitudinal side edges of the absorbent article is not transmitted to the side edges and thus will not cause the sides of the main body to slope downwardly.

Figure 8:
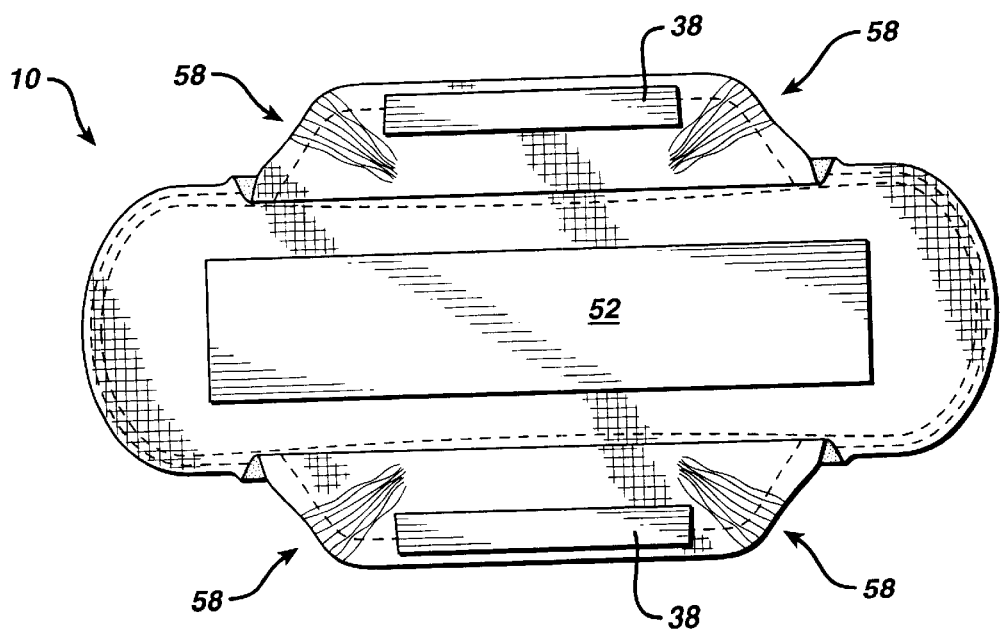
FIG. 8 is a bottom plan view of another embodiment of a sanitary napkin constructed in accordance with the present invention.

The base portion of each panel adjacent the proximal end 32 of each flap 34 is slightly shorter (dimension measured along a line transverse to the side edges of the main body 30) than the length of the main body. Preferably, the longitudinal dimension of the proximal end 32 is preferably from 50% to 90% of the length of the main body and is most preferably about 60% to 85% of the total length of the main body. The main body portion of the panel which forms the freely extending flaps in a region between the proximal portion and the distal portion tapers longitudinally from the base portion and is preferably from 25% to 75% of the length of the main body, most preferably between 30% to 50% of the length of the main body. For large flaps, it is preferred that the flap be longitudinally extensible to eliminate wrinkling and to permit the flaps to conformably adapt to the complex three dimensional shape of a crotch portion of a wearer's undergarment. In accordance with this aspect of the invention the flaps may comprise longitudinally elastic materials or as illustrated in FIG. 8, may contain slits of pleats 58 which permit the flap to conform to the crotch portion of an undergarment.

The juncture zone 36 is inwardly displaced with relation to the side edge by a distance which may vary in accordance with the intended application, provided, of course, that it is sufficiently inward to maintain at least a portion of the crotch portion of an undergarment beneath the main body and inward from the longitudinal side edges of the sanitary napkin. In a preferred embodiment, this distance is in the range from about ⅛ inch to about ½ inch. Most preferably this distance is about ⅛ inch. In addition the shape of the juncture zone may also vary in accordance with the intended application. For example, the juncture zone may comprise a series of discrete points of affixation. Thus, a plurality of juncture zones may be formed along the flap to affix the flap to the barrier layer at a plurality of spaced apart locations. In accordance with this aspect of the invention, one or more separate juncture zones may be located intermediate the respective opposite longitudinal end regions of the flaps. Alternatively, the juncture zone may comprise a single continuous seal which extends from one longitudinal end region to an opposite longitudinal end region of the flap.

The continuous seal line may be linear or curved. In a preferred embodiment, the continuous seal line comprises a curve having a shape which is a convex outward arcuate line with respect to a longitudinal centerline of the absorbent article.

As illustrated in FIGS. 3–6, the longitudinal dimension of the flaps 34 may optionally be such as to allow the flaps to overlap one another when they are folded about the undergarment. In order to retain the flaps in such overlapping condition they are provided with adhesive zones 38 on their barrier layer portions. In accordance with this aspect of the invention, when the flaps are folded and overlap one another the adhesive zone 38 on one flap is bonded to the cover layer portion of the other flap. Thus, the undergarment is completely encircled so it remains constantly in the gathered condition under the main body 30. It will also be appreciated that the positioning flaps also provide a stabilization function by preventing the main body 30 from becoming detached or moving freely with relation to the undergarment.

In an alternative embodiment hook and loop type fasteners (available under the brand VELCRO) may be used for connecting the flaps together. For example, the hook-type patch could be connected to the barrier layer portion of one flap while the loop-type patch is placed on the cover layer portion of the other flap.

As illustrated in FIGS. 10 and 11 flaps 34 need not completely encircle the crotch portion of the undergarment in order to provide the desired undergarment gathering effect under the main body 30. For example, flaps 34 may be adhesively adhered to the wearer's undergarment, or may be designed with shape retentive properties so when they are bent under the undergarment they do not have a tendency to return to their original configuration. One possibility is to incorporate in each flap 34 a malleable metallic insert (not shown), such as for example an aluminum wire, that when folded has the ability to resist deformation. The user would simply need to fold the flaps under the main body, so as to bend the malleable insert to gather and/or maintain the undergarment inward of the longitudinal edges of the main body. The resistance to deformation of the malleable insert would keep the flaps 34 in this position. Thus, the flaps 34 could be made shorter, since they do not need to connect with one another.

The sanitary napkin design, described above, has the effect of pinching the undergarment in the region of the flaps 34 while allowing the undergarment, particularly near the longitudinal extremities of the main body 30 to fan out. Thus, the undergarment is shaped as a bow-tie, the narrowest portion of the undergarment being located in the central region where the flaps 34 are. The length of this narrowest zone can be controlled by varying the width of the flaps 34; the wider the flaps the longer the narrowest zone will be. Some applications, such as sanitary napkins for heavy menstrual flows, could benefit from wide flaps that would retain a larger portion of the undergarment under the main body 30 in comparison to a design using narrow flaps.

In accordance with another embodiment of the invention, the flaps may be optionally provided with one or more panty edges gathering means. The panty edge gathering means provide a predetermined fold axis in the body of the flap about which the flap is preferentially folded over an edge portion of an undergarment. It should be noted that whatever panty edge gather means are employed, they are appreciably affixed to the layers of which the looping member 50 is formed in order to maintain the looping member 50 substantially unitized.

Figure 6:
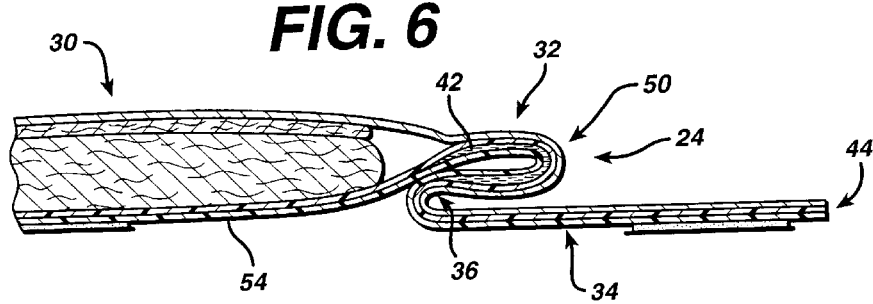
FIG. 6 is a cross-sectional view of another embodiment of a sanitary napkin constructed in accordance with the present invention taken along line 3—3 in FIG. 1.

Referring to FIG. 6, folding axis 40 is located laterally outward of proximal end 32 and juncture zone 36 thereby defining cavity 42. Cavity 42 may be sealed at opposite longitudinal end regions and filled with a fluid to provide a resilient, fluidly adaptive side edge margin. Suitable fluids include, but are not limited to one or a combination of the following fluidly adapting media: gases such as air, nitrogen and carbon dioxide, among others; liquids such as water and oils, among others, gels that are not too firm and than can flow in the fluidly adaptive component, and combinations of one or more of these media. The fluidly adaptive component may also contain, in addition to the fluid, some solid or semisolid substances or thixotropic gels. However, the nature and the amount of such substances should not be such as to prevent the fluid filled component from dynamically and transiently adapting to the contours of the user's body and clothing while the absorbent structure is being worn. It may be advantageous to use relatively high molecular weight which less easily diffuse through polymeric film materials.

Figure 4:
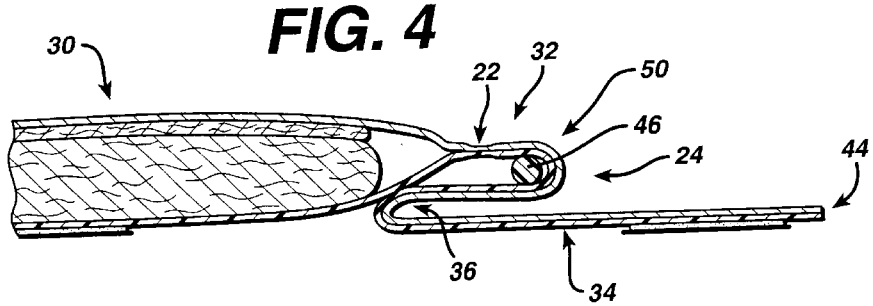
FIG. 4 is a cross-sectional view of another embodiment of a sanitary napkin constructed in accordance with the present invention taken along line 3—3 in FIG. 1.

Alternatively, or in addition to the presence of fluid in the cavity, as illustrated in FIG. 4, one or more elastic elements 46 may be affixed to an interior surface of the cavity. In accordance with this embodiment, the juncture zone 36 is located laterally inward from the longitudinal side edges of the absorbent article to provide a cavity. The presence of the cavity along the longitudinal side edges of an absorbent article a gasketing effect between the absorbent article and the thighs of the wearer of the article. One or more elastic strips 46 may be placed in the cavity, wherein the elastic strips 46 extend longitudinally along the side edges of the absorbent article adjacent to the absorbent core. Each strip of elastic 46 is preferably in an elastically contracted position and secured to the inside surface of the cavity i.e. to the inner surface of the flange such that they maintain the side flanges in an upward body-facing orientation and thus gather the longitudinal sides of the absorbent article into a curved configuration. In accordance with this embodiment, the elastic strips 46 may extend the entire length of the absorbent article and may be secured to the cover layer 12, the barrier layer 20 or both at a plurality of bond sites along the length of the absorbent article. The expedient of incorporating elastic members 46 into the lateral margins of absorbent products is more fully disclosed in U.S. Pat. No. 5,234,422 to Sneller et al., U.S. Pat. No. 5,074,856 to Coe et al., U.S. Pat. No. 5,032,121 to Mokry et al., and U.S. Pat. No. 4,770,657 to Ellis et al. which are incorporated herein by reference in their entirety.

Figure 5:
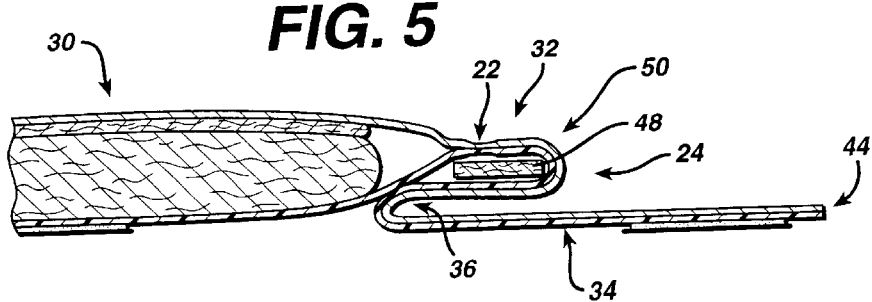
FIG. 5 is a cross-sectional view of another embodiment of a sanitary napkin constructed in accordance with the present invention taken along line 3—3 in FIG. 1.

Alternatively, as shown in FIG. 5, a thin strip of absorbent material 48 may be placed in the cavity 42 to provide protective side cuffs along the longitudinal sides of the absorbent article. In a preferred embodiment, the thin strip of absorbent material 48 comprises a highloft, resilient fibrous material which is capable of absorbing and retaining fluid.

Figure 7:
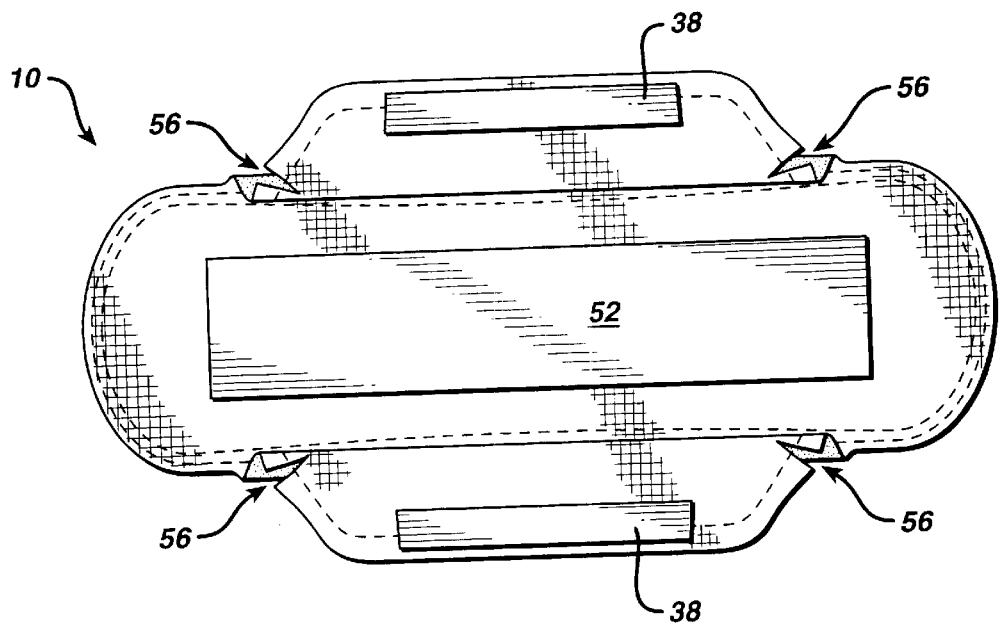
FIG. 7 is a bottom plan view of another embodiment of a sanitary napkin constructed in accordance with the present invention.
Figure 9:
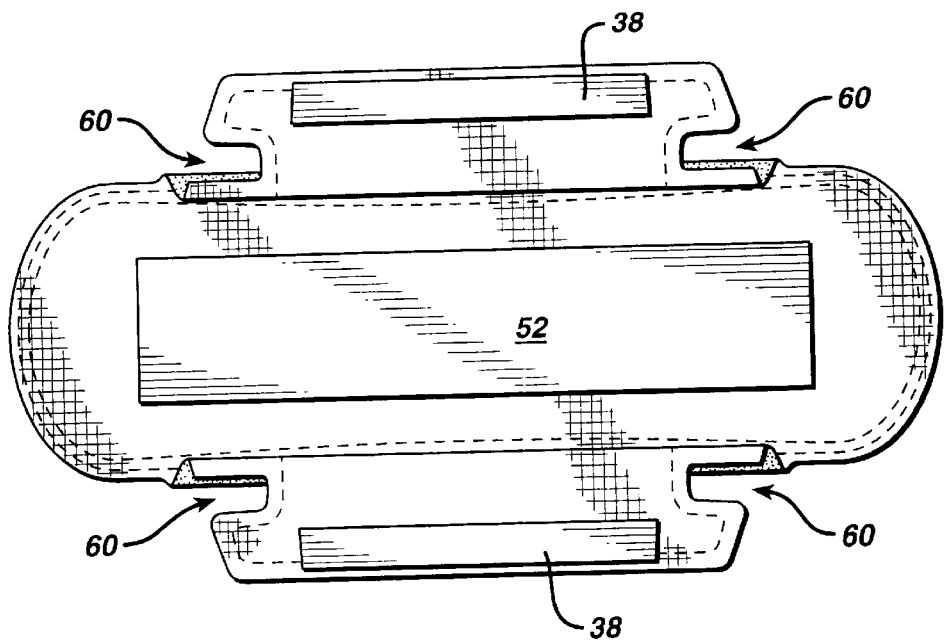
FIG. 9 is a bottom plan view of another embodiment of a sanitary napkin constructed in accordance with the present invention.

Referring to FIG. 7, slits or notches 56 may be optionally provided in the side edges of the flap 34 near the proximal end 32. Occasionally, the adhesive portion 38 of a flap 34 may become unattached from the surface to which it was secured. In such a case the edges of the crotch portion of the undergarment of the wearer may no longer be maintained gathered under the napkin. They may cause the flap to ride up the leg of the wearer or may contain the flap itself within the undergarment, in either the case the undergarment may become soiled. Slits 56 serve as an aid to prevent this from occurring should the adhesive indeed become unattached, as they are positioned to trap and retain the elastic edge portion of the panties should the adhesive not be affixed. An alternative slit configuration wherein the slips 60 are rectangular in shape is illustrated in FIG. 9.

In order to further enhance the stability of the sanitary napkin the main body 30 may be provided with adhesives, such as hot-melt adhesives capable of establishing a temporary bond with the undergarment material. These adhesives may be applied to the garment facing surface of the barrier layer 20 in various patterns, including complete adhesive coverage, parallel longitudinal lines, a line of adhesive following the perimeter of the structure, transverse lines of adhesive or the like. Alternatively, the sanitary napkin of this invention may be attached to a belt which encircles the waist of the wearer.

In accordance with the present invention there has also been provided a method of manufacturing the above described sanitary napkins comprising:

adhering an absorbent core to a surface of a fluid permeable cover layer wherein the cover layer has a width which is greater than the width of the absorbent core, covering the absorbent core with a fluid impervious barrier layer, wherein the barrier layer has a width substantially equivalent to the width of the cover layer, sealing the cover layer to the barrier layer around a peripheral edge margin of the absorbent core to form a flange seal, cutting the cover layer and the barrier layer outward of the flange seal in a pattern which provides a sanitary napkin having a pair of laterally extending flaps, one flap extending from each respective longitudinal side edge of the sanitary napkin, the flaps being integrally formed from the cover layer and the barrier layer, the flaps having a proximal end adjacent each respective longitudinal side edge of the sanitary napkin and a distal end extending laterally outward from the respective longitudinal side edge of the sanitary napkin, folding the flaps along a folding axis under the barrier layer, and affixing the flaps to the barrier layer along a juncture zone which is inward of the longitudinal side edges of the sanitary napkin such that the distal end of the flaps extend laterally inward toward a longitudinal centerline of the sanitary napkin.

The particular order of the above described process is not, per se, critical provided of course that the final product comprises an upper fluid permeable layer, a lower barrier layer and an absorbent layer between the upper layer and the lower layer. Accordingly, the step of affixing the flaps to the barrier layer may be performed prior to the step of cutting the cover and barrier layers. Similarly, the absorbent core may be adhered to the barrier layer prior to the cover layer. Thus, the only critical step in the present method is the expedient of affixing the integrally formed flaps to the barrier layer at the juncture zone.

Most preferably, the folding axis is an imaginary line parallel to a longitudinal side edge of the sanitary napkin and approximately centrally located within the flange seal and wherein the juncture zone affixes the flaps to at least a portion of the flange seal.

In a preferred embodiment, the method comprises forming the juncture zone laterally inward of the longitudinal side edge of the sanitary napkin thereby forming a cavity along the longitudinal edges of the sanitary napkin.

n accordance with another preferred embodiment, the process further comprises the steps of:

placing an elastic member in the cavity, tensioning the elastic member, and securing the elastic member along its length to the flange. The absorbent articles formed in accordance with this aspect of the invention have a curved shape which provides enhanced body fit.

Applications of the product and methods of the present invention for sanitary and other health-care uses can be accomplished by any sanitary protection, incontinence, medical and absorbent methods and techniques as are presently or prospectively known to those skilled in the art. Thus, it is intended that the present application covers the modifications and variations of this invention provided that they come within the scope of the appended claims and their equivalents.

I claim:

1. A sanitary absorbent article adapted to be worn in a crotch portion of an undergarment, comprising:
   (A) a main body having opposed longitudinal side edges and a longitudinal centerline, said main body including: a body-facing fluid-permeable upper layer intended for placement against a perineal region of a wearer, a garment-facing fluid-impervious lower layer, and an absorbent layer between the upper layer and the lower layer; and
   (B) a first panel and a second panel, each panel being integrally formed from both the upper layer and the lower layer, each panel having a proximal end adjacent to and extending from respective opposite longitudinal side edges of said main body and a distal end freely extending laterally from the proximal end of said panel, the proximal end and the distal end defining therebetween a body portion, the body portion further comprising a longitudinally extending folding axis which is substantially parallel to said longitudinal side edge, each panel being capable of being folded about said folding axis onto itself such that the distal end of the panel projects laterally inward towards the longitudinal centerline of said main body on a garment-facing side of the sanitary absorbent article, each panel further including:
   (i) a juncture zone located within the body portion adjacent the proximal end of said panel, the juncture zone attaching a portion of said panel to the lower layer inwardly from the longitudinal side edge of said main body, the juncture zone simultaneously defining a looping member and a freely extending flap
   (ii) the looping member being adjacent to and substantially parallel with the longitudinal side edges of the main body and being defined by a portion of the body portion of said panel between the proximal end and the juncture zone and including the folding axis therebetween;
   (iii) each flap being defined by a portion of the body portion of said panel between the juncture zone and the distal end and being capable of being folded about a side edge of the crotch portion of the undergarment, each flap further including a first transverse end and a second transverse end, the second transverse end being opposite the first transverse end and defining therebetween a flap width in a direction substantially parallel to the longitudinal side edges of the main body,
   (iv) each flap having means for holding at least a portion of one edge of the undergarment inwardly of said longitudinal side edge of the main body when the flap is in a folded condition about the side edge of the undergarment, wherein the juncture zone of the first panel is separated from the juncture zone of said second panel by a distance which defines an undergarment allowance and the undergarment allowance, as measured at the respective transverse ends of the flaps, the distance being adapted to gather the edges of the undergarment inward toward the longitudinal centerline of the main body in an amount less than 25% of an original width of the undergarment when each flap is in the folded condition.

2. A sanitary article as defined in claim 1, wherein the juncture zone comprises a series of discrete points of attachment.

3. A sanitary absorbent article as defined in claim 1, wherein the juncture zone comprises a longitudinally extending continuous line of attachment extending from one end of each respective flap to the opposite end of each respective flap.

4. A sanitary absorbent article as defined in claim 3, wherein the continuous line of attachment is arcuate having a convex inward orientation with respect to the longitudinal centerline of the main body.

5. A sanitary absorbent article as defined in claim 1, wherein the juncture zone of each panel is in vertical registration with at least a portion of the absorbent layer.

6. A sanitary absorbent article as defined in claim 1, wherein the juncture zone of each panel is located underneath the absorbent layer.

7. A sanitary absorbent article as defined in claim 6, wherein the folding axis is adjacent to the flange seal and the juncture zone is located laterally inward of the respective folding axis of each panel thereby defining a cavity that extends along the longitudinal edges of said main body.

8. A sanitary absorbent article as defined in claim 7, wherein the juncture zone extends longitudinally along the entire length of the flange seal and wherein the cavity extends along the longitudinal sides of said main body.

9. A sanitary absorbent article as defined in claim 8, wherein the cavity contains an elastic member, the elastic member being in tension and secured along its length to the flange seal.

10. A sanitary absorbent article as defined in claim 8, wherein the cavity is free of elastic material.

11. A sanitary absorbent article as defined in claim 8, wherein the cavity contains a strip of absorbent material extending longitudinally along at least a portion of the longitudinal side edge of said main body.

12. A sanitary absorbent article as defined in claim 11, wherein the strip of absorbent material extends longitudinally along substantially the entire longitudinal side edge of said main body.

13. A sanitary absorbent article as defined in claim 1, wherein the juncture zone of each panel is bonded to the lower layer by adhesive.

14. A sanitary absorbent article as defined in claim 1, wherein the juncture zone of each panel is bonded to the lower layer by thermal bonding.

15. A sanitary absorbent article as defined in claim 1, wherein said flaps have a length sufficient to permit said flaps to be folded around a crotch portion of an undergarment and to be adhered to each other.

16. A sanitary absorbent article as defined in claim 1, wherein said main body has a length measured along its longitudinal centerline, wherein said flaps have a width measured along an imaginary axis parallel to the longitudinal edges of said main body and along the juncture zone where said panels are attached to the fluid impervious lower layer, and wherein the width of said panels is from 10% to 90% the length of said main body.

17. A sanitary absorbent article as defined in claim 1, wherein the sanitary absorbent article is a sanitary napkin.

18. A sanitary absorbent article as defined in claim 1, wherein at least one of said flaps includes an adhesive zone located on a side of the flap that faces the undergarment when said flap is folded about the undergarment, the adhesive zone being capable of establishing a releasable bond with an underside of the garment when said flap is folded about the undergarment.

19. A sanitary napkin as defined in claim 1, wherein each freely extending flap and each looping member is formed exclusively from a portion of said upper layer and a portion of said lower layer.

20. A sanitary napkin as defined in claim 19, wherein said portion of said upper layer and said portion of said lower layer forming each freely extending flap and each looping member are arranged in surface to surface abutment along an entire length of said freely extending flap and said looping member.

21. A sanitary napkin as defined in claim 1, wherein a distance between said juncture zone of said first panel and said juncture zone of said second panel is at least 71 mm apart.

22. A sanitary napkin as defined in claim 21, wherein said distance between said juncture zone of said first panel and said juncture zone of said second panel is between 75 mm and 85 mm apart.

* * * * *